(12) United States Patent
Yoo et al.

(10) Patent No.: US 11,083,434 B2
(45) Date of Patent: Aug. 10, 2021

(54) ULTRASONIC IMAGING APPARATUS AND CONTROL METHOD THEREOF

(71) Applicant: SAMSUNG MEDISON CO., LTD., Gangwon-Do (KR)

(72) Inventors: Jun Sang Yoo, Seongnam-si (KR); Kwang-Hee Lee, Incheon (KR); Soo In Cho, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 978 days.

(21) Appl. No.: 14/792,410

(22) Filed: Jul. 6, 2015

(65) Prior Publication Data

US 2016/0051230 A1 Feb. 25, 2016

(30) Foreign Application Priority Data

Aug. 25, 2014 (KR) .................. 10-2014-0110583

(51) Int. Cl.
*A61B 8/00* (2006.01)
*A61B 8/08* (2006.01)
(Continued)

(52) U.S. Cl.
CPC .............. *A61B 8/463* (2013.01); *A61B 8/085* (2013.01); *A61B 8/466* (2013.01); *A61B 8/469* (2013.01);
(Continued)

(58) Field of Classification Search
CPC .............................. A61B 6/5223; A61B 8/483
See application file for complete search history.

(56) References Cited

U.S. PATENT DOCUMENTS

2003/0153823 A1* 8/2003 Geiser ................... G06T 7/0012
600/407
2007/0110321 A1* 5/2007 Okada ................ G06K 9/00228
382/209
(Continued)

FOREIGN PATENT DOCUMENTS

EP 2238913 A1 10/2010
JP 2013-123582 A 6/2013
(Continued)

OTHER PUBLICATIONS

Korean Notice of Patent Allowance dated Jul. 6, 2016 issued in Korean Patent Application No. 10-2014-0110583 (English translation).

(Continued)

*Primary Examiner* — Jason M Ip
(74) *Attorney, Agent, or Firm* — Morgan, Lewis & Bockius LLP

(57) ABSTRACT

Disclosed herein are an ultrasonic imaging apparatus of successively displaying a plurality of slice images of an object at predetermined frame rate, and a control method of the ultrasonic imaging apparatus. According to an embodiment of the ultrasonic imaging apparatus, the ultrasonic imaging apparatus may include: an image processor configured to extract a target in an object based on volume data of the object; a controller configured to determine a region of interest in the object, based on the extracted target; and a display unit configured to successively display a plurality of slice images of the object, including the region of interest.

18 Claims, 23 Drawing Sheets

(51) Int. Cl.
  *G01S 7/52* (2006.01)
  *G01S 15/89* (2006.01)
(52) U.S. Cl.
  CPC ............ *A61B 8/483* (2013.01); *A61B 8/5223* (2013.01); *A61B 8/5253* (2013.01); *A61B 8/54* (2013.01); *G01S 7/52063* (2013.01); *G01S 7/52073* (2013.01); *G01S 7/52074* (2013.01); *G01S 7/52084* (2013.01); *G01S 15/8993* (2013.01); *A61B 8/4405* (2013.01); *A61B 8/4427* (2013.01); *A61B 8/4472* (2013.01); *A61B 8/468* (2013.01); *A61B 8/523* (2013.01); *A61B 8/56* (2013.01)

(56) References Cited

U.S. PATENT DOCUMENTS

| | | | |
|---|---|---|---|
| 2008/0114244 | A1 | 5/2008 | Murashita et al. |
| 2009/0082668 | A1 | 3/2009 | Hamada et al. |
| 2009/0267940 | A1 | 10/2009 | Garg et al. |
| 2012/0288172 | A1 | 11/2012 | Perrey et al. |
| 2012/0293514 | A1* | 11/2012 | Virtue ................... G06T 7/174 345/424 |
| 2012/0296214 | A1 | 11/2012 | Urabe et al. |
| 2013/0012820 | A1 | 1/2013 | Brown et al. |
| 2013/0229504 | A1 | 9/2013 | Cheng |
| 2014/0225892 | A1* | 8/2014 | Parma ................... G06T 7/0012 345/426 |

FOREIGN PATENT DOCUMENTS

| | | |
|---|---|---|
| KR | 10-2007-0041825 A | 4/2007 |
| KR | 10-2011-0026547 A | 3/2011 |
| KR | 10-2011-0039932 A | 4/2011 |
| WO | 2009/044316 A1 | 4/2009 |
| WO | 2013/055611 A1 | 4/2013 |

OTHER PUBLICATIONS

Extended European Search Report dated Jan. 21, 2016 issued in European Patent Application No. 15174049.5.
Korean Office Action dated Oct. 29, 2015 issued in Korean Patent Application No. 10-2014-0110583 (English translation).
E. Merz, "Current 3D/4D ultrasound technology in prenatal diagnosis," Eur. Clinics Obstet. Gynaecol (2005), vol. 1, pp. 184-193.
K. Y. Leung, et al., "Three-dimensional extended imaging: a new display modality for three-dimensional ultrasound xamination," Ultrasound Obstet Gyneocol 2005, vol. 26, pp. 244-251.
P. S. Hiremath, et al., "Follicle Detection and Ovarian Classification in Digital Ultrasound Images of Ovaries," Intech, Advancement and Breakthroughs in Ultrasound Imaging, Chapter 7, 2013, pp. 168-199.
T. Chen, et al., "Automatic ovarian follicle quantification from 3D ultrasound data using global/local context with database guided segmentation," Siemens Corporation Research, Princeton, NJ.
I. Jorgner, et al., "SonoAvC Studies on automated detection and measurements of hyper-stimulated follicles utilizing a new algorithm," GE Healthcare.
European Office Action dated Jul. 24, 2019 issued in European Patent Application No. 15174049.5.

* cited by examiner

ULTRASONIC IMAGING APPARATUS AND CONTROL METHOD THEREOF

CROSS-REFERENCE TO RELATED APPLICATION

This application claims the benefit of Korean Patent Application No. 10-2014-0110583, filed on Aug. 25, 2014 in the Korean Intellectual Property Office, the disclosure of which is incorporated herein by reference.

BACKGROUND

1. Field

Embodiments of the present disclosure relate to an ultrasonic imaging apparatus for creating an image of an object using ultrasonic waves, and a control method of the ultrasonic imaging apparatus.

2. Description of the Related Art

An ultrasonic imaging apparatus is medical equipment of irradiating ultrasonic signals toward a target inside an object from the surface of the object, and receiving ultrasonic signals (that is, ultrasonic echo signals) reflected from the target so as to non-invasively acquire slice images about soft tissue of the object or images about blood vessels of the object based on information of the ultrasonic echo signals.

The ultrasonic imaging apparatus has advantages that it is a compact, low-priced apparatus compared to other medical imaging apparatuses, such an X-ray imaging apparatus, a Computerized Tomography (CT) scanner, a Magnetic Resonance Image (MRI) apparatus, and a nuclear medicine diagnosis apparatus, and it can display images in real time. Also, the ultrasonic imaging apparatus has high safety since there is no risk for patients to be exposed to radiation. For the advantages, the ultrasonic imaging apparatus is widely used to diagnose the heart, breasts, abdomen, urinary organs, uterus, etc.

Particularly, in obstetrics and gynecology, the ultrasonic imaging apparatus is used to check the number of follicles in a uterus in order to diagnose polycystic ovary syndrome which is one cause of sterility.

SUMMARY

Therefore, it is an aspect of the present disclosure to provide an ultrasonic imaging apparatus for successively displaying a plurality of slice images of an object at predetermined frame rate, and a control method of the ultrasonic imaging apparatus.

Additional aspects of the disclosure will be set forth in part in the description which follows and, in part, will be obvious from the description, or may be learned by practice of the disclosure.

In accordance with one aspect of the present disclosure, an ultrasonic imaging apparatus includes: an image processor configured to extract a target in an object based on volume data of the object; a controller configured to determine a region of interest in the object, based on the extracted target; and a display unit configured to successively display a plurality of slice images of the object, including the region of interest.

The display unit may highlight the extracted target in the plurality of slice images of the object.

The display unit may display the region of interest as a section in the plurality of slice images.

The display unit may successively display a plurality of slice images of the object for an entire section of the object, the entire section of the object decided by the volume data of the object, and if a slice image being currently displayed includes the region of interest, the display unit may stop successively displaying the plurality of slice images of the object for the entire section of the object.

After stopping successively displaying the plurality of slice images of the object for the entire section of the object, the display unit may successively display a plurality of slice images of the object for a section of interest that is decided by the region of interest.

The controller may determine the region of interest based on a size of the extracted target.

The controller may determine, as the region of interest, a region satisfying a predetermined condition in the remaining area of the object not extracted as the target.

The display unit may display the plurality of slice images of the object, including the region of interest, at the same time.

The ultrasonic imaging apparatus may further include an input unit configured to receive at least one command of a command for determining the region of interest as the target, and a command for cancelling the extracted target.

The display unit may successively display a plurality of first slice images of the object, including the region of interest, wherein the plurality of first slice images may be perpendicular to a predetermined first direction.

The display unit may mark a position of a first slice image being currently displayed, in a second slice image of the object, wherein the second slice image of the object may be perpendicular to a second direction being perpendicular to the first direction.

The display unit may mark the position of the first slice image being currently displayed, in a third slice image of the object, wherein the third slice image of the object may be perpendicular to a third direction being perpendicular to the first direction and the second direction.

The display unit may mark a position of a slice image being currently displayed, in a 3Dimensional (3D) image of the object.

In accordance with one aspect of the present disclosure, a method of controlling an ultrasonic imaging apparatus includes: extracting a target in an object based on volume data of the object; determining a region of interest in the object, based on the extracted target; and successively displaying a plurality of slice images of the object, including the region of interest.

The successively displaying of the plurality of slice images of the object, including the region of interest, may include highlighting the extracted target in the plurality of slice images of the object.

The successively displaying of the plurality of slice images of the object, including the region of interest, may include displaying the region of interest as a section in the plurality of slice images.

The method may further include: successively displaying a plurality of slice images of the object for an entire section of the object, the entire section of the object decided by the volume data of the object, and if a slice image being currently displayed includes the region of interest, stopping successively displaying the plurality of slice images of the object for the entire section of the object.

The successively displaying of the plurality of slice images of the object, including the region of interest, may include, after stopping successively displaying the plurality of slice images of the object for the entire section of the object, successively displaying a plurality of slice images of the object for a section of interest that is decided by the region of interest.

The determining of the region of interest in the object may include determining the region of interest based on a size of the extracted target.

The determining of the region of interest in the object may include determining, as the region of interest, a region satisfying a predetermined condition in the remaining area of the object not extracted as the target.

The method may further include displaying the plurality of slice images of the object, including the region of interest, at the same time, according to an input from a user.

The method may further include determining the region of interest as the target or cancelling the extracted target, according to an input from a user.

The successively displaying of the plurality of slice images of the object, including the region of interest, may include successively displaying a plurality of first slice images of the object, including the region of interest, wherein the plurality of first slice images may be perpendicular to a predetermined first direction.

The successively displaying of the plurality of slice images of the object, including the region of interest, may include marking a position of a first slice image being currently displayed, in a second slice image of the object, wherein the second slice image of the object may be perpendicular to a second direction being perpendicular to the first direction.

The successively displaying of the plurality of slice images of the object, including the region of interest, may include marking the position of the first slice image being currently displayed, in a third slice image of the object, wherein the third slice image of the object may be perpendicular to a third direction being perpendicular to the first direction and the second direction.

The successively displaying of the plurality of slice images of the object, including the region of interest, may include marking a position of a slice image being currently displayed, in a 3Dimensional (3D) image of the object.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
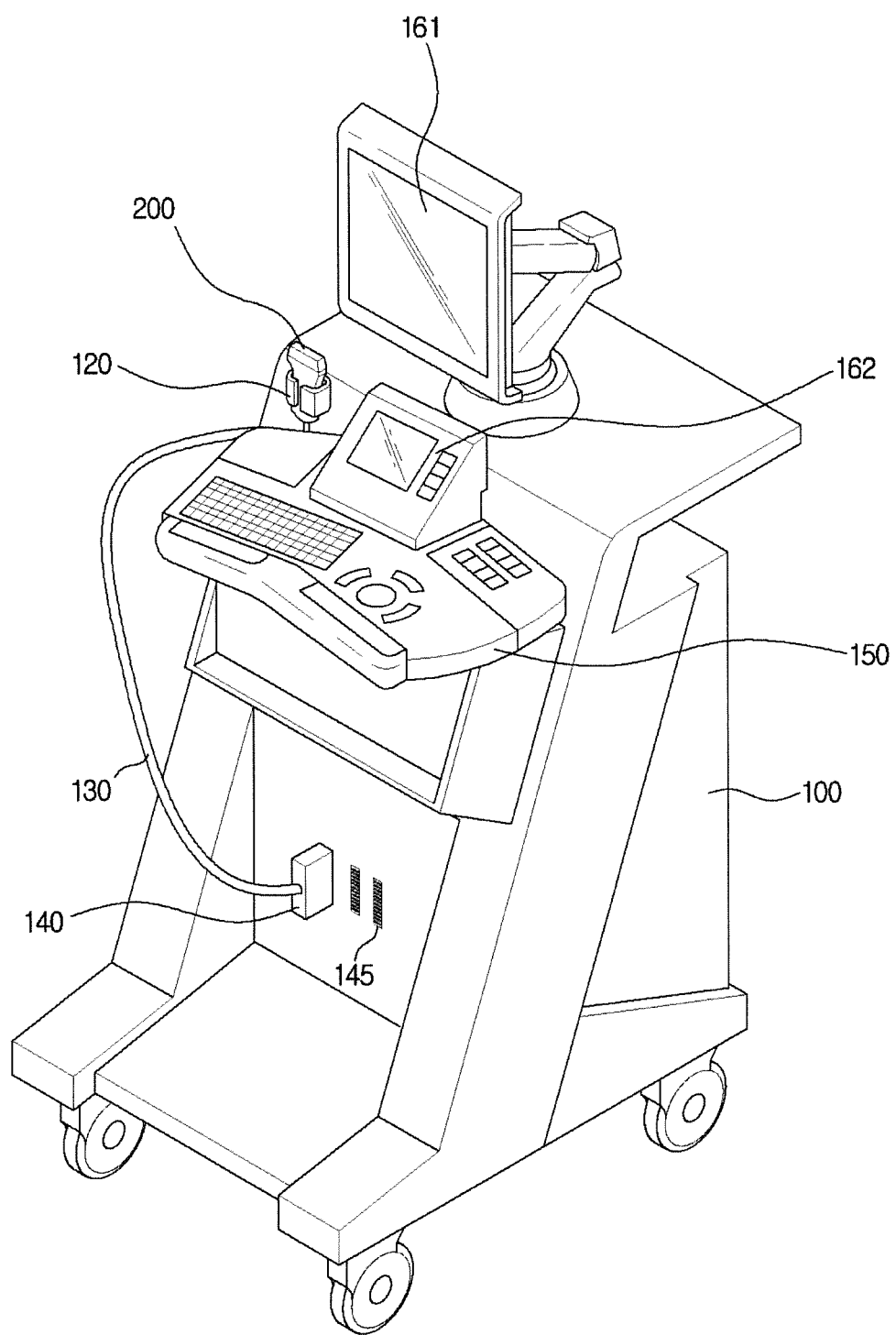
FIG. 1 is a perspective view of an ultrasonic imaging apparatus according to an embodiment of the present disclosure.

Reference will now be made in detail to the embodiments of the present disclosure, examples of which are illustrated in the accompanying drawings, wherein like reference numerals refer to like elements throughout.

Hereinafter, an ultrasonic imaging apparatus and a control method thereof according to embodiments of the present disclosure will be described in detail with reference to the accompanying drawings.

In the following description, an "ultrasound image" means an image of an object acquired using ultrasonic waves. Also, the "object" means a human body, an animal, a metal, a nonmetal, or a part thereof. For example, the object may include vessels or organs, such as a liver, a heart, a uterus, a brain, breasts, abdomen, etc. Also, the object may include a phantom, and the phantom means a material having a volume that is very close to an effective atomic number and a density of a living body.

Also, in the following description, a "target" may be a part of an object, which a user wants to examine through an ultrasound image.

Also, in the following description, a "user" may be a medical professional, such as a doctor, a nurse, a medical technologist, or a medical imaging professional, or may be a technician that repairs medical equipment, although not limited to them.

FIG. 1 is a perspective view of an ultrasound imaging apparatus according to an embodiment of the present disclosure. Referring to FIG. 1, the ultrasound imaging apparatus may include a main body 100, an ultrasound probe 200, an input unit 150, and a display unit 160.

In one side of the main body 100, one or more female connectors 145 may be provided. A male connector 140 connected to a cable 130 may be physically coupled with one of the female connectors 145.

Meanwhile, at the bottom of the main body 100, a plurality of castors (not shown) may be provided to move the ultrasound imaging apparatus. The plurality of castors may fix the ultrasound imaging apparatus at a specific location or move the ultrasound imaging apparatus in a specific direction. The ultrasound imaging apparatus is called a cart-type ultrasound imaging apparatus.

However, the ultrasound imaging apparatus may be a portable ultrasound imaging apparatus that can be possessed by a user even when he/she moves to a long distance. The portable ultrasound imaging apparatus may not include castors. Examples of such a portable ultrasound imaging apparatus include a Picture Archiving and Communication System (PACS) viewer, a smart phone, a laptop computer, PDA, and a tablet PC, although not limited to these.

The ultrasound probe 200 may contact the surface of an object to transmit and receive ultrasonic waves. More specifically, the ultrasound probe 200 may transmit ultrasonic waves to the inside of an object according to a transmission signal received from the main body 100, receive echo ultrasonic waves reflected from a specific part inside the object, and then transfer the received echo ultrasonic waves to the main body 100.

The ultrasound probe 200 may be connected to one end of the cable 120, and the other end of the cable 130 may be connected to the male connector 140. The male connector 140 connected to the other end of the cable 130 may be physically coupled with the female connector 145 of the main body 100.

Alternatively, the ultrasound probe 200 may be connected to the main body 100 in a wireless fashion. In this case, the ultrasound probe 200 may transmit echo ultrasonic waves received from an object to the main body 100 in the wireless fashion. Also, a plurality of ultrasound probes may be connected to the main body 100.

Meanwhile, in the main body 100, an image processor 300 (see FIG. 2) for converting echo ultrasonic waves received from the ultrasound probe 200 into an ultrasound image may be provided. The image processor 300 may be implemented in the form of hardware such as a microprocessor, or in the form of software that can be executed on hardware.

The image processor 300 may perform scan conversion on echo ultrasonic waves to create an ultrasound image. The ultrasound image may be a gray sale image acquired by scanning an object in Amplitude mode (A-mode), Brightness mode (B-mode) or Motion mode (M-mode), or a Doppler image that represents a moving object using the Doppler effect. The Doppler image may include a blood flow Doppler image (or called a color Doppler image) showing flow of blood, a tissue Doppler image showing movement of a tissue, and a spectral Doppler image showing moving speed of an object as a waveform.

The image processor 300 may extract B-mode components from echo ultrasonic waves received by the ultrasound probe 200 in order to create a B-mode image. The image processor 300 may create an ultrasound image in which intensity of echo ultrasonic waves is represented to be bent, based on the B-mode components.

Likewise, the image processor 300 may extract Doppler components from echo ultrasonic waves, and create a Doppler image in which movement of an object is represented as a color or waveform, based on the Doppler components.

Also, the image processor 300 may perform volume rendering on volume data acquired through echo ultrasonic waves to create a 3Dimensional (3D) ultrasound image, or create an elastic image resulting from imaging a degree of deformation of an object according to pressure. In addition, the image processor 300 may represent various additional information in the form of text or graphic images on the ultrasound image.

Meanwhile, the ultrasound image may be stored in an internal memory of the main body 100 or in an external memory. Alternatively, the ultrasound image may be stored in a web storage or a cloud server that performs a storage function on the web.

The input unit 150 is used to receive commands related to operations of the ultrasound imaging apparatus. For example, the input unit 150 may receive a mode selection command for selecting a mode, such as an A mode, a B mode, a M mode, or a Doppler mode. Also, the input unit 150 may receive a diagnosis start command.

A command input through the input unit 150 may be transferred to the main body 100 through wired/wireless communication.

The input unit 150 may include at least one of a keyboard, a foot switch, and a foot pedal. The keyboard may be hardwarily implemented, and disposed on the upper part of the main body 100. The keyboard may include at least one(s) of a switch, keys, a joystick, and a trackball. As another example, the keyboard may be softwarily implemented as a graphic user interface (GUI). In this case, the keyboard may be displayed through a sub display unit 162 or a main display unit 161. The foot switch or the foot pedal may be provided in the lower part of the main body 100, and a user may control operations of the ultrasonic imaging apparatus using the foot pedal.

The display unit 160 may include the main display unit 161 and the sub display unit 162.

The sub display unit 162 may be mounted on the main body 100. In FIG. 1, the sub display unit 162 is provided over the input unit 150. The sub display unit 162 may display an application related to operation of the ultrasonic imaging apparatus. For example, the sub display unit 162 may display menus or guidance needed for ultrasonic diagnosis. The sub display unit 162 may be, for example, a Cathode Ray Tube (CRT) or a Liquid Crystal Display (LCD).

The main display unit 161 may be also mounted on the main body 100. In FIG. 1, the main display unit 161 is positioned over the sub display unit 162. The main display unit 161 may display ultrasonic images acquired during ultrasonic diagnosis according to an input received through the input unit 150. Like the sub display unit 162, the main display unit 161 may also be, for example, a CRT or a LCD. In FIG. 1, the main display unit 161 is coupled with the main body 100, however, the main display unit 161 may be removably coupled with the main body 100.

Also, in FIG. 1, a case in which the ultrasonic imaging apparatus includes both the main display unit 161 and the sub display unit 162 is shown, however, the sub display unit 162 may be omitted. In this case, an application, a menu, etc., which are displayed through the sub display unit 162, may be displayed through the main display unit 161.

Meanwhile, the ultrasound imaging apparatus may further include a communication unit. The communication unit may connect to a network in a wired/wireless fashion to communicate with an external device or a server. The communication unit may receive/transmit data from/to a hospital server or other medical apparatuses in a hospital, connected through Picture Archiving and Communication System (PACS). Also, the communication unit may perform data communication according to a Digital Imaging and Communications in Medicine (DICOM) standard.

The communication unit may transmit/receive data related to diagnosis of an object, such as an ultrasound image, echo ultrasonic waves, and Doppler data of the object, through the network. Also, the communication unit may transmit/receive medical images photographed by another medical apparatus, such as a CT scanner, a MRI apparatus, an X-ray apparatus, etc., through the network. In addition, the communication unit may receive information about a patient's diagnosis history, therapeutic schedule, etc., from a server, and use the information for diagnosis of an object. Furthermore, the communication unit may perform data communication with a doctor's or patient's mobile terminal, as well as a server or a medical apparatus in a hospital.

The communication unit may connect to the network in a wired/wireless fashion to receive/transmit data from/to a server, a medical apparatus, or a mobile terminal. The communication unit may include one or more components to enable communications with external devices, and may include a short-range communication module, a wired communication module, and a mobile communication module.

The short-range communication module may be a module for short-range communication within a predetermined distance. The short-range communication may be Wireless LAN (WLAN), Wireless-Fidelity (Wi-Fi), Bluetooth, Zigbee, Wi-Fi Direct (WFD), Ultra Wideband (UWB), Infrared Data Association (IrDA), Bluetooth Low Energy (BLE), or Near Field Communication (NFC), although the short-range communication is not limited to these.

The wired communication module may be a module for communication based on electrical signals or optical signals, and may be a pair cable, a coaxial cable, an optical fiber cable, or an Ethernet cable.

The mobile communication module may transmit/receive radio signals from/to at least one of a base station, an external terminal, and a server over a mobile communication network. Herein, the radio signals may include voice call signals, video call signals, or various kinds of data according to text/multimedia message transmission/reception.

Figure 2:
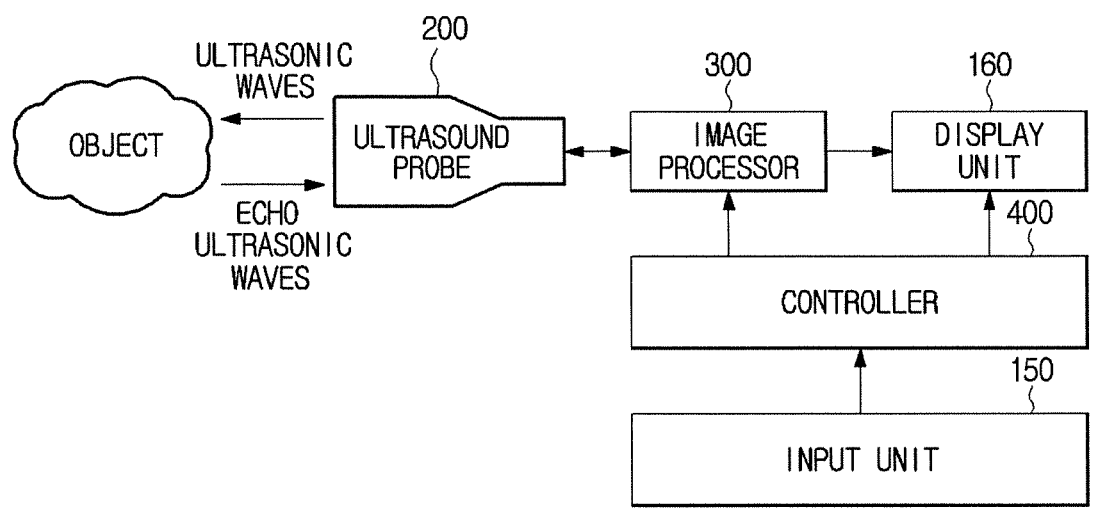
FIG. 2 is a control block diagram of an ultrasonic imaging apparatus according to an embodiment of the present disclosure.

FIG. 2 is a control block diagram of an ultrasonic imaging apparatus according to an embodiment of the present disclosure;

Referring to FIG. 2, an ultrasonic imaging apparatus according to an embodiment of the present disclosure may include an ultrasound probe 200 configured to transmit and receive ultrasonic waves to acquire volume data of an object; an image processor 300 configured to create an ultrasound image of the object based on the volume data of the object; a display unit 160 configured to display the ultrasound image; an input unit 150 configured to receive a control command from a user; and a controller 400 configured to control overall operations of the ultrasonic imaging apparatus.

The ultrasound probe 200 may irradiate ultrasonic signals to an object, and receive echo ultrasonic waves reflected from the object. Since ultrasonic waves are reflected with different degrees of reflectance according to medium, the ultrasound probe 200 may acquire information about the inside of an object by collecting echo ultrasonic waves reflected from the object.

The ultrasound probe 200 may be implemented in various ways within the technical concept of acquiring volume data of an object. For example, if the transducer elements of the ultrasound probe 200 has a 1 Dimensional (1D) arrangement, the ultrasound probe 200 may acquire volume data according to a freehand method. Also, the ultrasound probe 200 may acquire volume data according to a mechanical method, without having to receive a user's manipulation. If the transducer elements of the ultrasound probe 200 has a 2Dimensional (2D) arrangement, the ultrasound probe 200 may acquire volume data by controlling the transducer elements.

The image processor 300 may create an ultrasound image of the object using the volume data of the object. At this time, the image processor 300 may create 3D ultrasound images of the object, as well as 2D ultrasound images about sections of the object.

In order to create a 3D ultrasound image, the image processor 300 performs volume rendering on the volume data. The image processor 300 may volume-render the 3D volume data using one of volume rendering methods well-known in the art. In detail, volume rendering may be classified into surface rendering and direct volume rendering.

The surface rendering is to extract surface information from volume data based on predetermined scalar values and amounts of spatial changes, to convert the surface information into a geometric factor, such as a polygon or a surface patch, and then to apply a conventional rendering technique to the geometric factor. Examples of the surface rendering are a marching cubes algorithm and a dividing cubes algorithm.

The direct volume rendering is to directly render volume data without converting volume data into a geometric factor. The direct volume rendering is useful to represent a translucent structure since it can visualize the inside of an object as it is. The direct volume rendering may be classified into an object-order method and an image-order method according to a way of approaching volume data.

The image-order method is to sequentially decide pixel values of an image. An example of the image-order method is volume ray casting. The object-order method is to directly project volume data on an image. An example of the object-order method is splatting.

Also, the image processor 300 may extract a target from volume data. For example, if an object is a human's uterus and targets are follicles in the uterus, the image processor 300 may extract follicles using volume data.

The image processor 300 may be implemented in various ways within the technical concept of extracting a target inside an object based on volume data. For example, the image processor 300 may extract, as a target, a volume data region having brightness values that are within a predetermined range. Also, the image processor 300 may extract a target by determining whether or not the size of a volume data region having predetermined brightness values is within a predetermined range.

The display unit 160 may display the ultrasound image created by the image processor 300. More specifically, the display unit 160 may display a slice image or a 3D image of the object created by the image processor 300, or may display the slice image and the 3D image of the object together.

At this time, the display unit 160 may highlight a target extracted from the slice image being displayed. For example, the display unit 160 may change the color or shade of an area corresponding to the target, or may change the color or shade of the boundary line of the area corresponding to the target. Alternatively, the display unit 160 may display a marker indicating a location of the area corresponding to the target.

Hereinafter, a method in which the display unit 160 displays ultrasound images under the control of the controller 400 will be described in detail.

The controller 400 may control the display unit 160 to successively display a plurality of slice images of an object for an entire section of the object decided by volume data of the object. The display unit 160 may successively display a plurality of slice images of the object for the entire section of the object, at predetermined frame rate, under the control of the controller 400.

Herein, the entire section of the object means a section of the object that can be displayed as slice images by acquired volume data. A distance between two successive slice images of the object and the predetermined frame rate may be decided by a user's input or by the internal computation of the ultrasonic imaging apparatus.

As such, by displaying a plurality of slice images of the object for the entire section of the object, information about the inside of the object can be provided to a user, and also by scanning the inside of the object, the user can determine a region of interest which will be described.

Hereinafter, a method of displaying a plurality of slice images of an object for an entire section of the object will described.

Figure 3A:
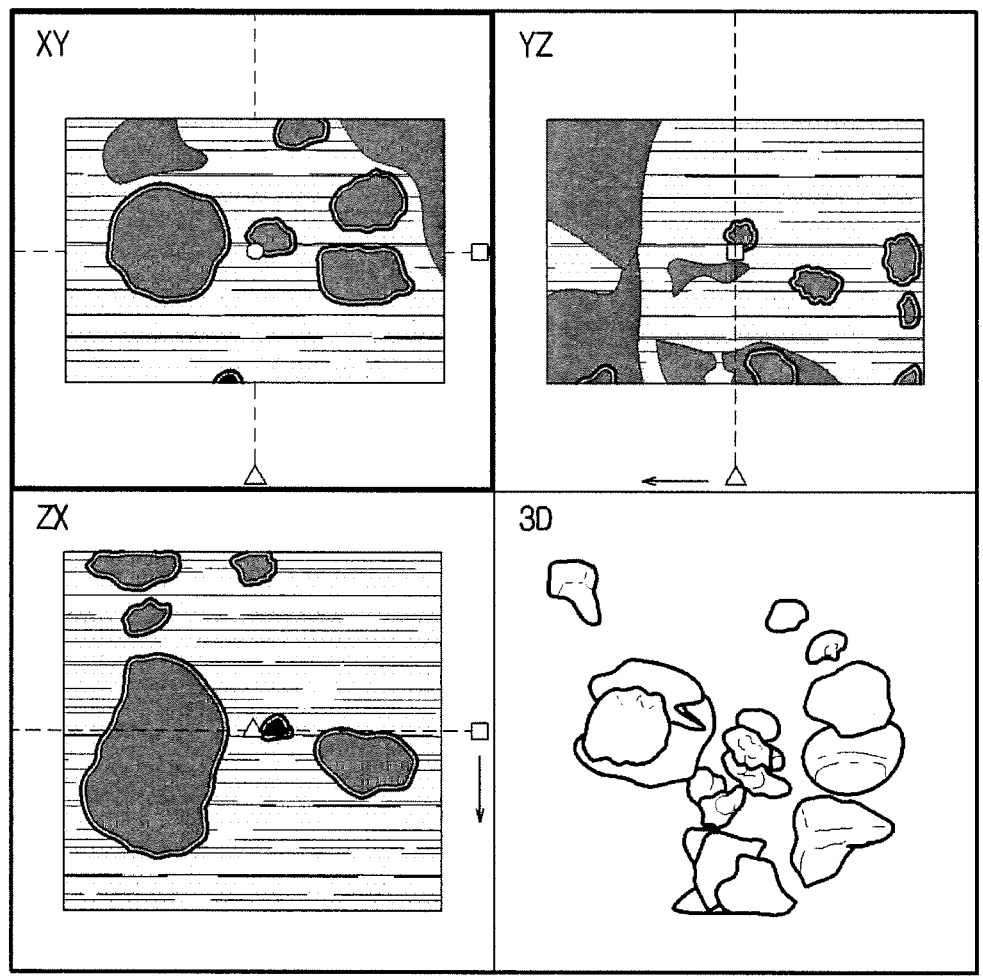
FIGS. 3A to 3C are views for describing an embodiment of a method of successively displaying a plurality of slice images of an object for an entire section of the object, in an ultrasonic imaging apparatus according to an embodiment of the present disclosure.
Figure 3B:
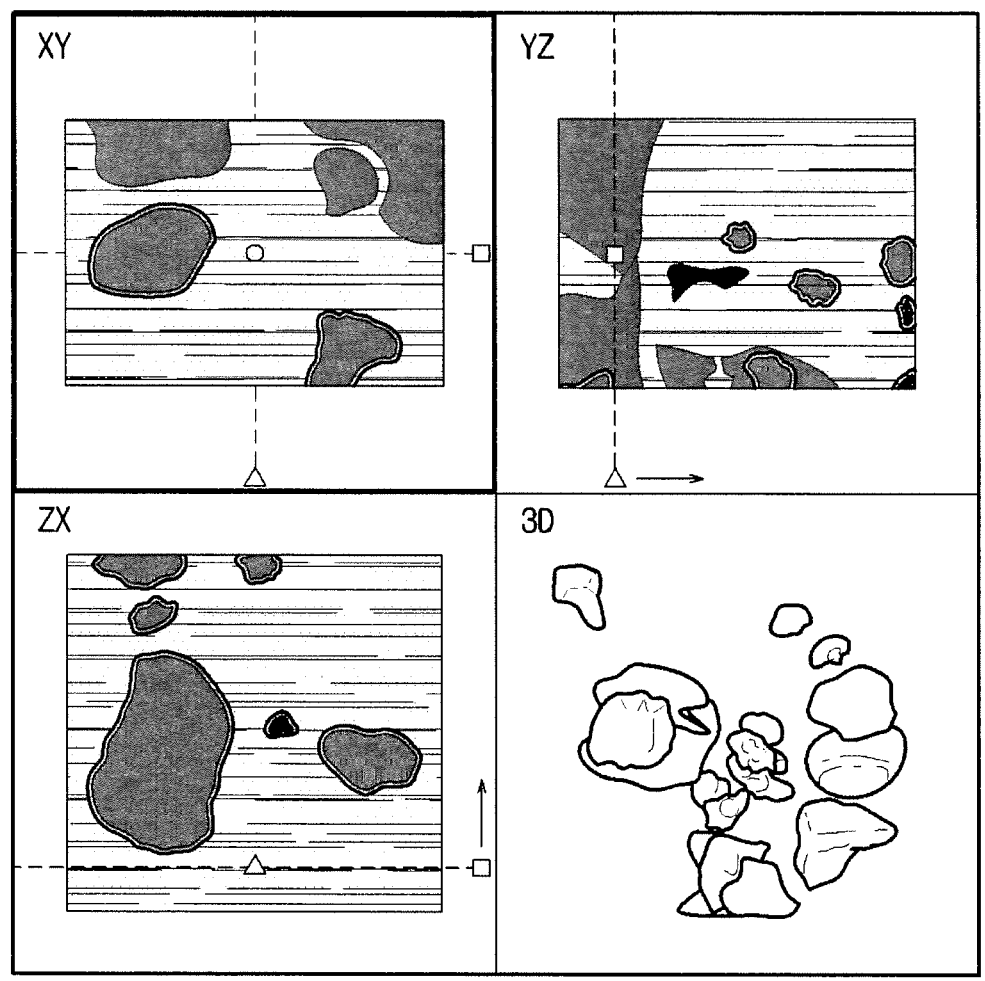
Figure 3C:
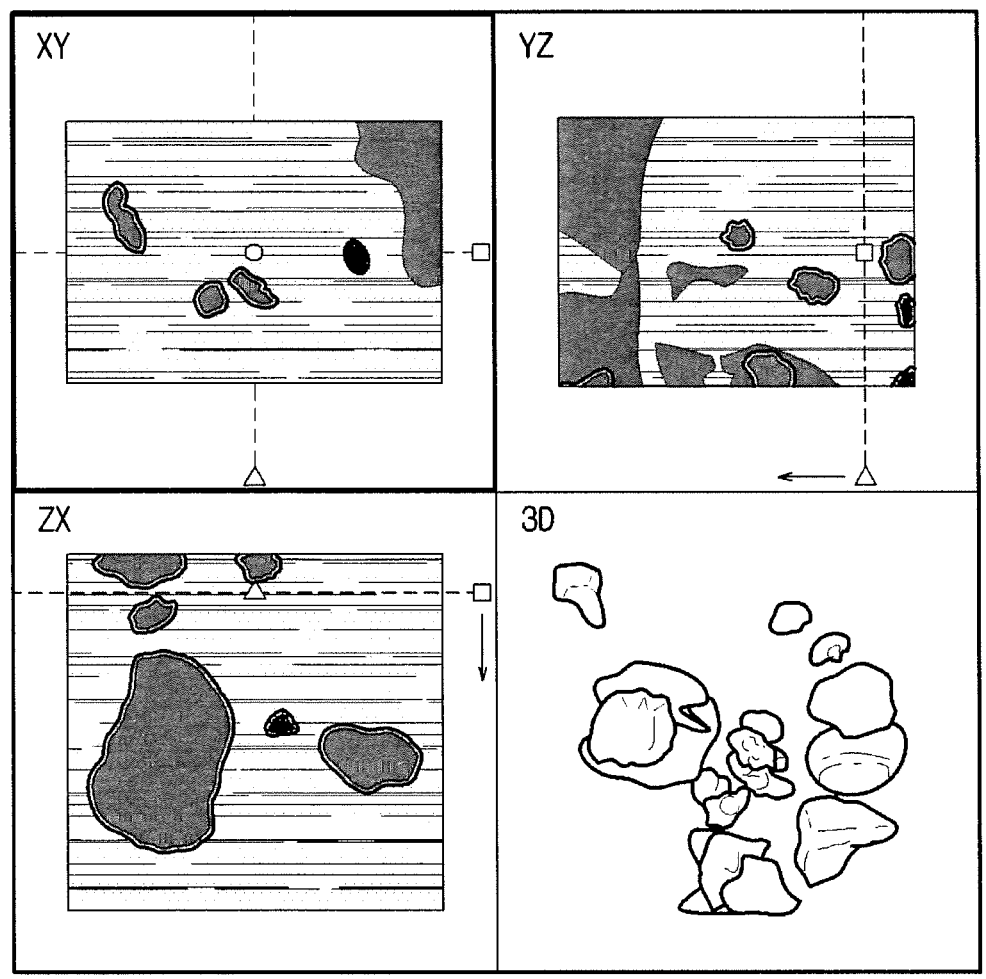

FIGS. 3A to 3C are views for describing an embodiment of a method of successively displaying a plurality of slice images of an object for an entire section of the object, in an ultrasonic imaging apparatus according to an embodiment of the present disclosure.

Hereinafter, for convenience of description, a direction in which ultrasonic waves are irradiated to an object is assumed to be a z-axis direction, and directions which are perpendicular to the z-axis direction and which are perpendicular to each other are assumed to be an x-axis direction and a y-axis direction. Specifically, in a 1D array probe, a direction in which elements are aligned is assumed to be an x-axis direction, and in a 2D array probe, a direction in which elements are arranged is assumed to be an x-axis direction, and another direction in which the elements are arranged is assumed to be a y-axis direction.

Also, the z-axis direction is assumed to be a first direction, the x-axis direction is assumed to be a second direction, and the y-axis direction is assumed to be a third direction.

Referring to FIG. 3A to 3C, the controller 400 may control the display unit 160 to successively display a plurality of slice images of an object, which are perpendicular to a predetermined first direction, for an entire section of the object. More specifically, the controller 400 may control the display unit 160 to successively display a plurality of slice images (also referred to as a plurality of first slice images) of an object, which are perpendicular to a first direction, at predetermined frame rate.

Referring to FIGS. 3A to 3C, the display unit 160 may successively display a plurality of first slice images. In the respective first slice images, the same target is represented by different areas with different boundary lines. Accordingly, a user can easily recognize a shape and size of the target.

Meanwhile, the controller 400 may control the display unit 160 to successively mark positions of the plurality of first slice images respectively in a plurality of slice images (also referred to as a plurality of second slice images) of the object, the second slice images being perpendicular to a second direction.

Referring to FIGS. 3A to 3C, the display unit 160 may display the second slice images to the right of the first slice images, wherein the second slice images are parallel to the yz plane. More specifically, the display unit 160 may display a marker indicating a position of a first slice image being currently displayed, in a second slice.

With elapse of time from FIG. 3A to FIG. 3C, as the first slice images are successively changed and displayed at the predetermined frame rate, the locations of markers displayed in the second slice images are also changed.

As such, by successively displaying the first slice images and simultaneously providing the second slice images in which the positions of the first slice images are respectively marked, the display unit 160 can help a user accurately recognize a location and shape of the target.

In addition, the controller 400 may control the display unit 160 to successively display a plurality of slice images (also referred to as a plurality of third slice images) which are perpendicular to a third direction and in which the positions of the plurality of first slice images are respectively marked.

Referring to FIGS. 3A to 3C, the display unit 160 may display the third slice images below the first slice images, wherein the third slice images are parallel to the zx plane. More specifically, the display unit 160 may display a marker indicating a position of a first slice image being currently displayed, in a third slice.

With elapse of time from FIG. 3A to FIG. 3C, as the first slice images are successively changed and displayed at the predetermined frame rate, the locations of markers displayed in the third slice images are also changed.

Figure 4A:
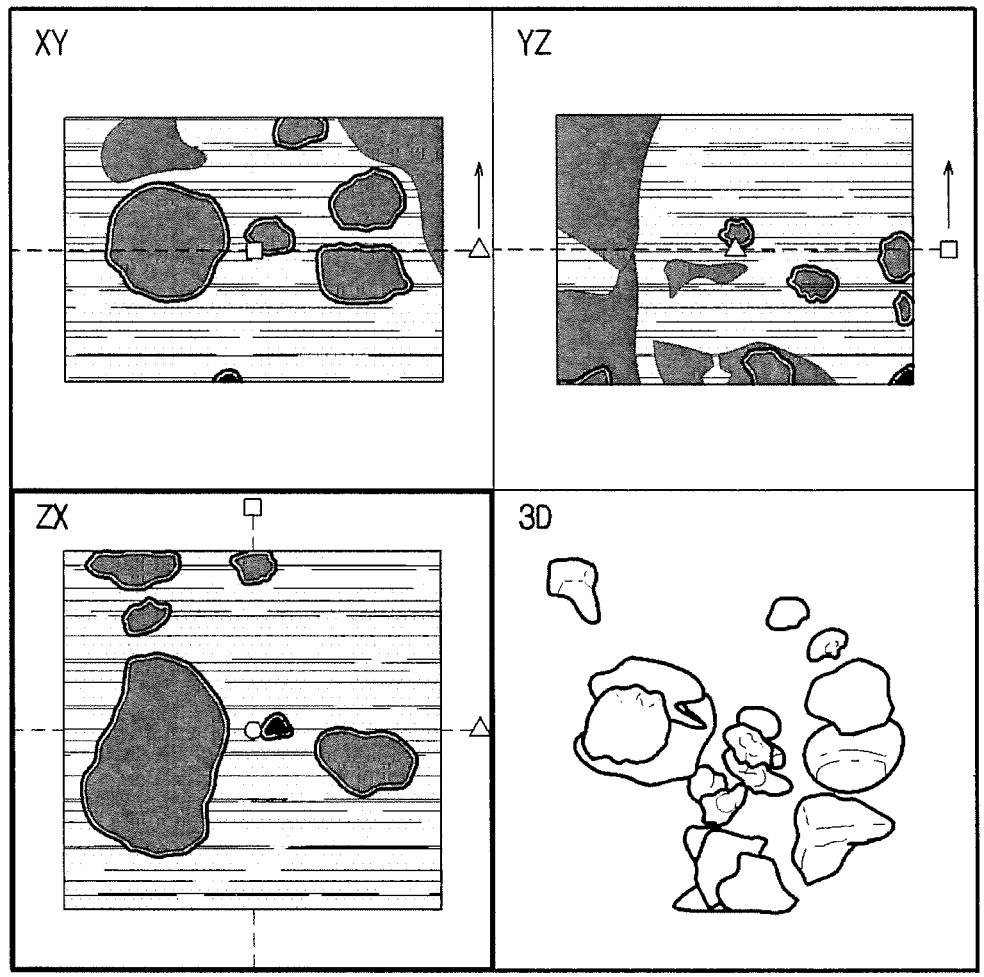
FIGS. 4A to 4C are views for describing another embodiment of a method of successively displaying a plurality of slice images of an object for an entire section of the object, in an ultrasonic imaging apparatus according to an embodiment of the present disclosure.
Figure 4B:
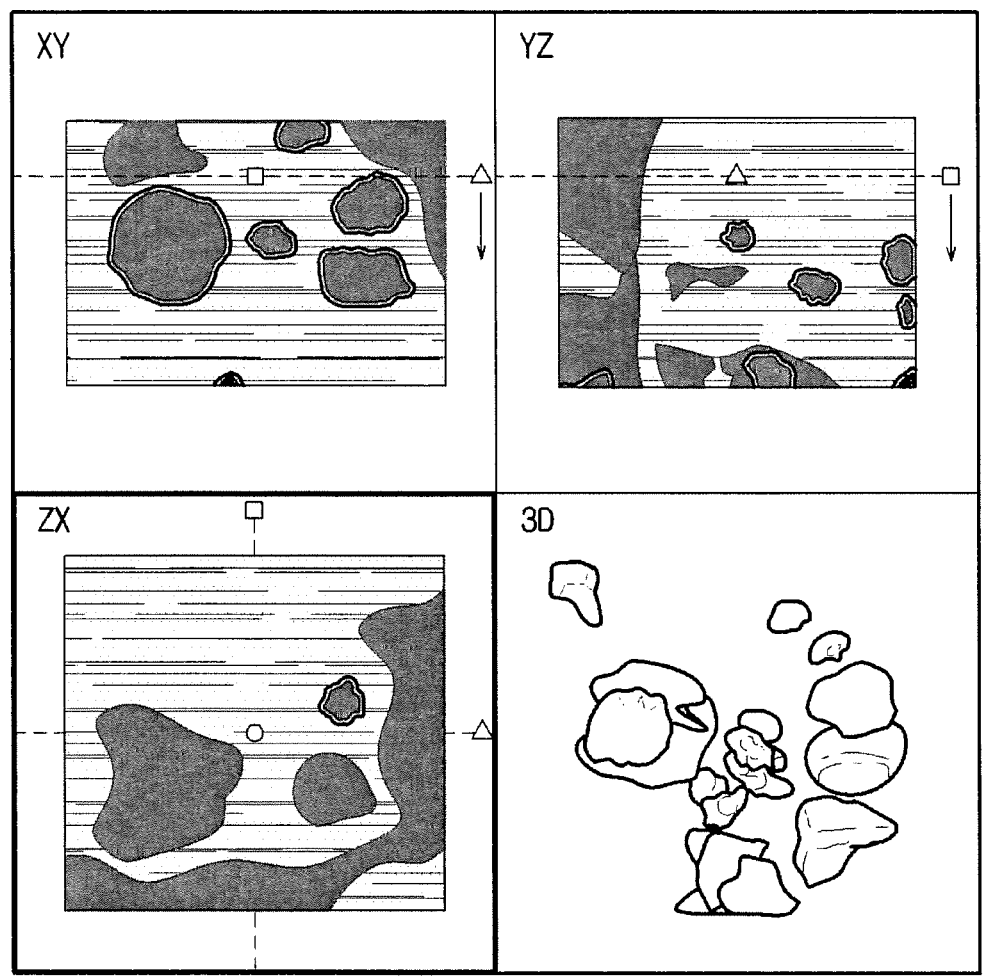
Figure 4C:
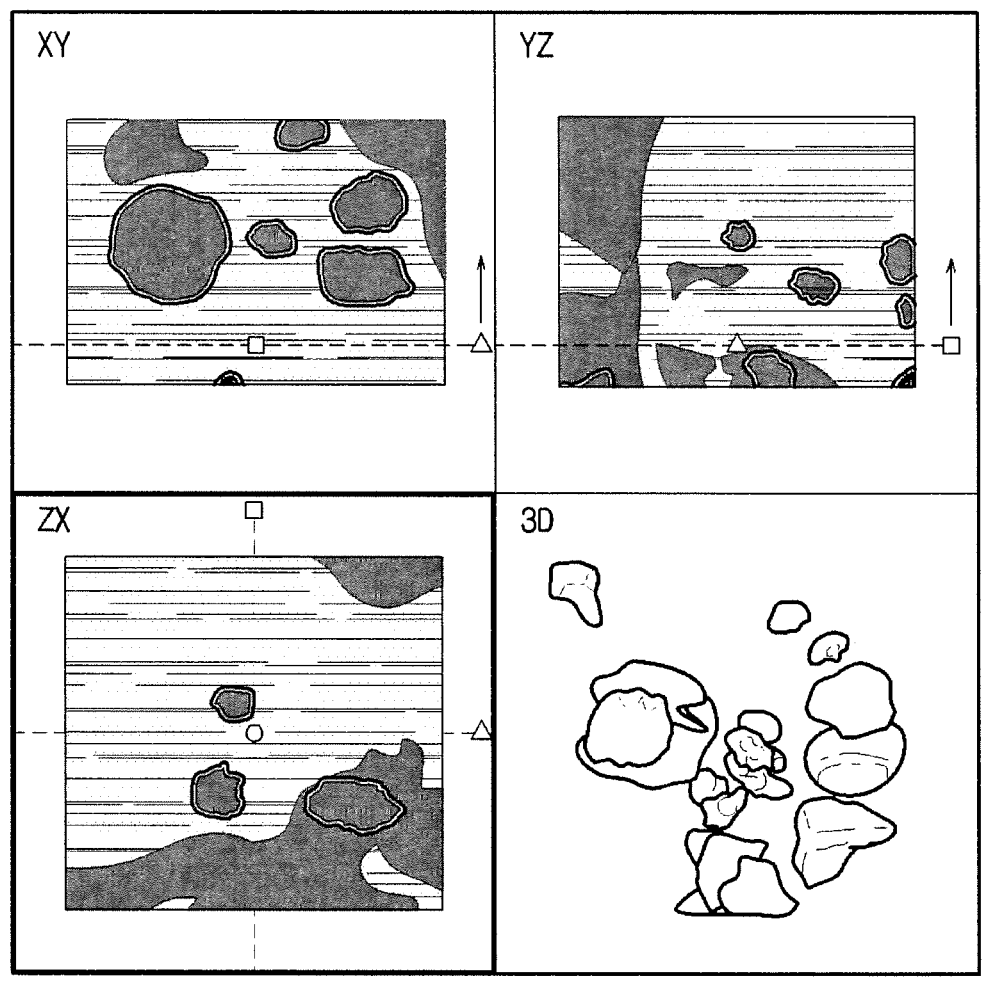

FIGS. 4A to 4C are views for describing another embodiment of a method of successively displaying a plurality of slice images of an object for an entire section of the object, in an ultrasonic imaging apparatus according to an embodiment of the present disclosure.

Unlike the embodiment shown in FIGS. 3A to 3C, the controller 400 may control the display unit 160 to successively display a plurality of slice images of an object, which are perpendicular to a second direction, for an entire section of the object. More specifically, the controller 400 may control the display unit 160 to successively display a plurality of slice images (also referred to as a plurality of second slice images) of an object, which are parallel to the yz plane being perpendicular to the x-axis, at predetermined frame rate.

Also, the controller 400 may control the display unit 160 to display a first slice image or a third slice image in which a marker indicating a position of a second slice image being currently displayed is displayed.

Referring to FIGS. 4A to 4C, the display unit 160 may successively display the second slice images at predetermined frame rate. Simultaneously, the display unit 160 may display a plurality of first slice images and a plurality of third slice images in which the positions of the second slice images being successively displayed are marked.

As such, by successively providing a plurality of slice images of a target acquired in various directions, and marking the position of each slice image in the other slice images, the display unit 160 can help a user accurately recognize a shape and location of the target.

Figure 5A:
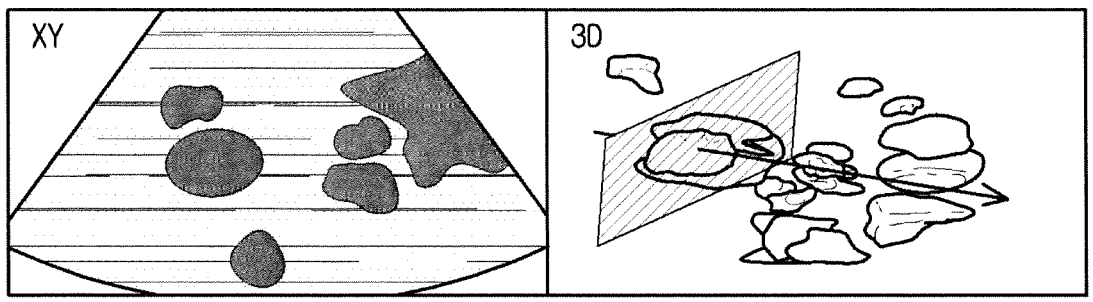
FIGS. 5A to 5C are views for describing another embodiment of a method of successively displaying a plurality of slice images of an object for an entire section of the object, in an ultrasonic imaging apparatus according to an embodiment of the present disclosure.
Figure 5B:
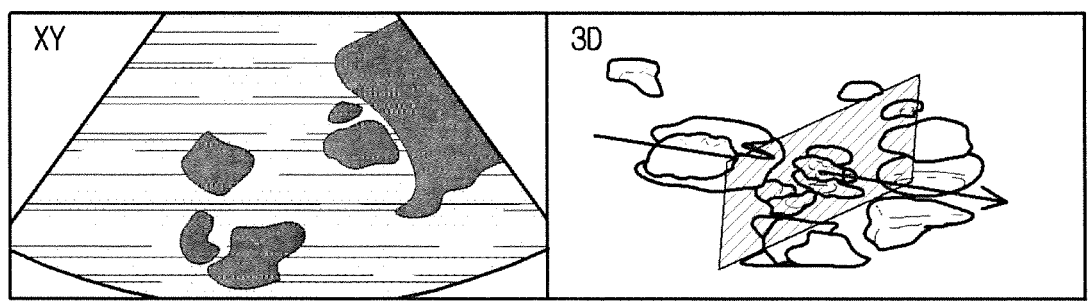
Figure 5C:
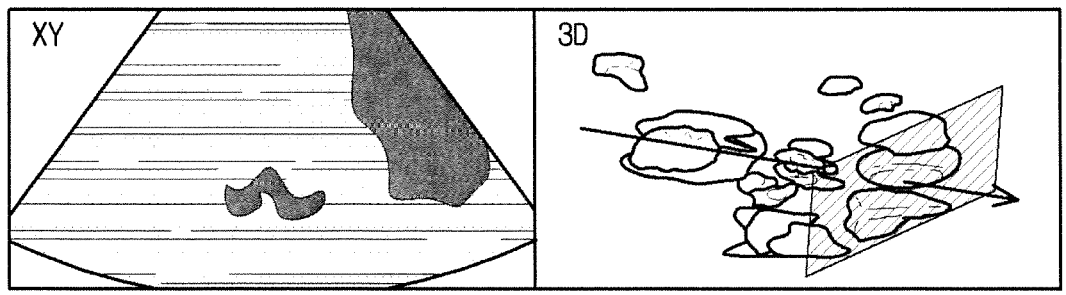

FIGS. 5A to 5C are views for describing another embodiment of a method of successively displaying a plurality of slice images of an object for an entire section of the object, in an ultrasonic imaging apparatus according to an embodiment of the present disclosure.

The controller 400 may control the display unit 160 to successively display positions of a plurality of slice images of an object respectively in a plurality of 3D images of the object, for the entire section of the object.

For example, the controller 400 may control the display unit 160 to successively display a plurality of first slice images of an object at predetermined frame rate, while successively displaying positions of the first slice images being currently displayed, respectively, in a plurality of 3D images of the object. More specifically, the controller 400 may display a marker indicating a position of a first slice image of an object being displayed on the display unit 160, in a 3D image of the object.

As a result, the display unit 160 may successively display the plurality of first slice images of the object at the predetermined frame rate, and simultaneously display a plurality of 3D images of the object in which the positions of the first slice images are marked, as shown in FIGS. 5A to 5C.

In FIGS. 5A to 5C, a case in which a plurality of first slice images of an object are successively displayed is shown, however, a plurality of second or third slice images of an object may be successively displayed together with a plurality of 3D images of the object. Alternatively, at least two kinds of slice images among first slice images, second slice images, and third slice images of an object may be displayed together with 3D images of the object.

As such, by marking a position of a target slice image being displayed in a 3D image of the target, the display unit 160 can help a user accurately recognize a shape and location of the target.

Also, when the display unit 160 displays a plurality of slice images for an entire section of an object, the display unit 160 may detect a region of interest from a slice image. At this time, the controller 400 may control the display unit 160 to stop successively displaying the plurality of slice images for the entire section of the object.

The controller 400 may determine the region of interest based on targets extracted by the image processor 300 (see FIG. 2). The region of interest may be a region that needs to be additionally examined by a user in the extracted targets or the other area.

For example, the controller 400 may determine a target satisfying a predetermined condition among the extracted targets, as a region of interest. If the extracted targets are follicles, the controller 400 may determine the largest target among the extracted targets as a region of interest so that a user can examine the largest follicle among the extracted follicles.

As another example, the controller 400 may determine a region satisfying a predetermined condition in the remaining area not extracted as targets, as a region of interest. When follicles are extracted as targets, there may be a follicle not extracted through volume data. The controller 400 may determine a region satisfying a predetermined condition from a slice image, as a region of interest, to allow a user to determine whether or not the region of interest is a follicle.

The predetermined condition for determining a region of interest may have been decided in advance by a user's input or by the internal computation of the ultrasonic imaging apparatus.

Figure 6A:
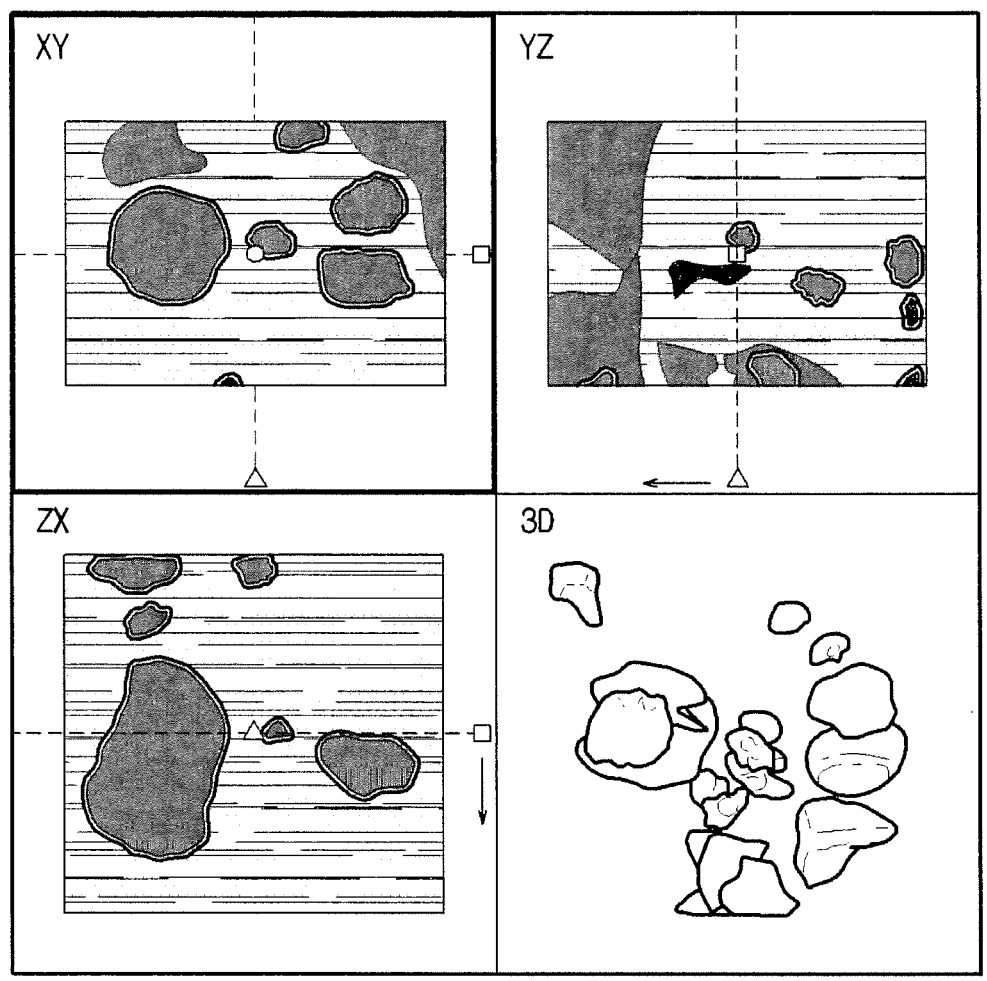
FIGS. 6A and 6B are views for describing an embodiment of a method of stopping successively displaying a plurality of slice images in an ultrasonic imaging apparatus according to an embodiment of the present disclosure.
Figure 6B:
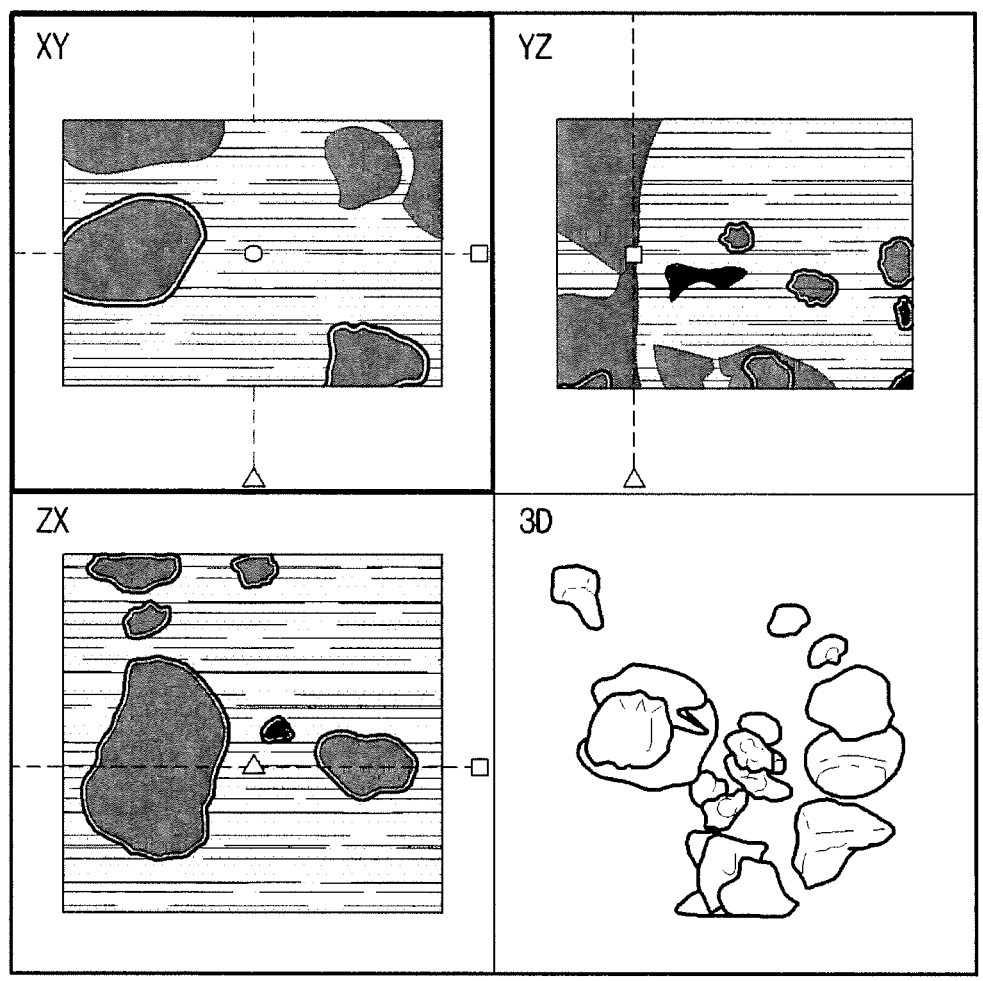

FIGS. 6A and 6B are views for describing an embodiment of a method of stopping successively displaying a plurality of slice images in an ultrasonic imaging apparatus according to an embodiment of the present disclosure. In the embodiment as shown in FIGS. 6A and 6B, a region of interest is assumed to be a region satisfying a predetermined condition in an area not extracted as a target.

As described above with reference to FIGS. 3A to 3C, the display unit 160 may successively display a plurality of first slice images for an entire section of an object, at predetermined frame rate. At this time, if a first slice image includes a region of interest, the display unit 160 may stop successively displaying the plurality of first slice images in order to keep displaying the first slice image including the region of interest.

For example, referring to FIG. 6A, the display unit 160 may successively display a plurality of first slice images. At this time, if a first slice image displayed on the display unit 160 includes a region of interest, the display unit 160 may stop successively displaying the plurality of first slice images to keep displaying the first slice image including the region of interest.

In FIG. 6B, a region of interest is assumed to be a region satisfying a predetermined condition in an area not extracted as a target.

Since the display unit 160 keeps displaying the first slice image including the region of interest, a user can determine whether there is a target not extracted by the image processor 300.

After the display unit 160 stops successively displaying the plurality of slice images of the object for the entire section of the object, the controller 400 may control the display unit 160 to successively display a plurality of slice images of the object for a section of interest that is decided by the region of interest.

A distance between two successive slice images of the object and the predetermined frame rate may be decided by a user's input or by the internal computation of the ultrasonic imaging apparatus.

Figure 7A:
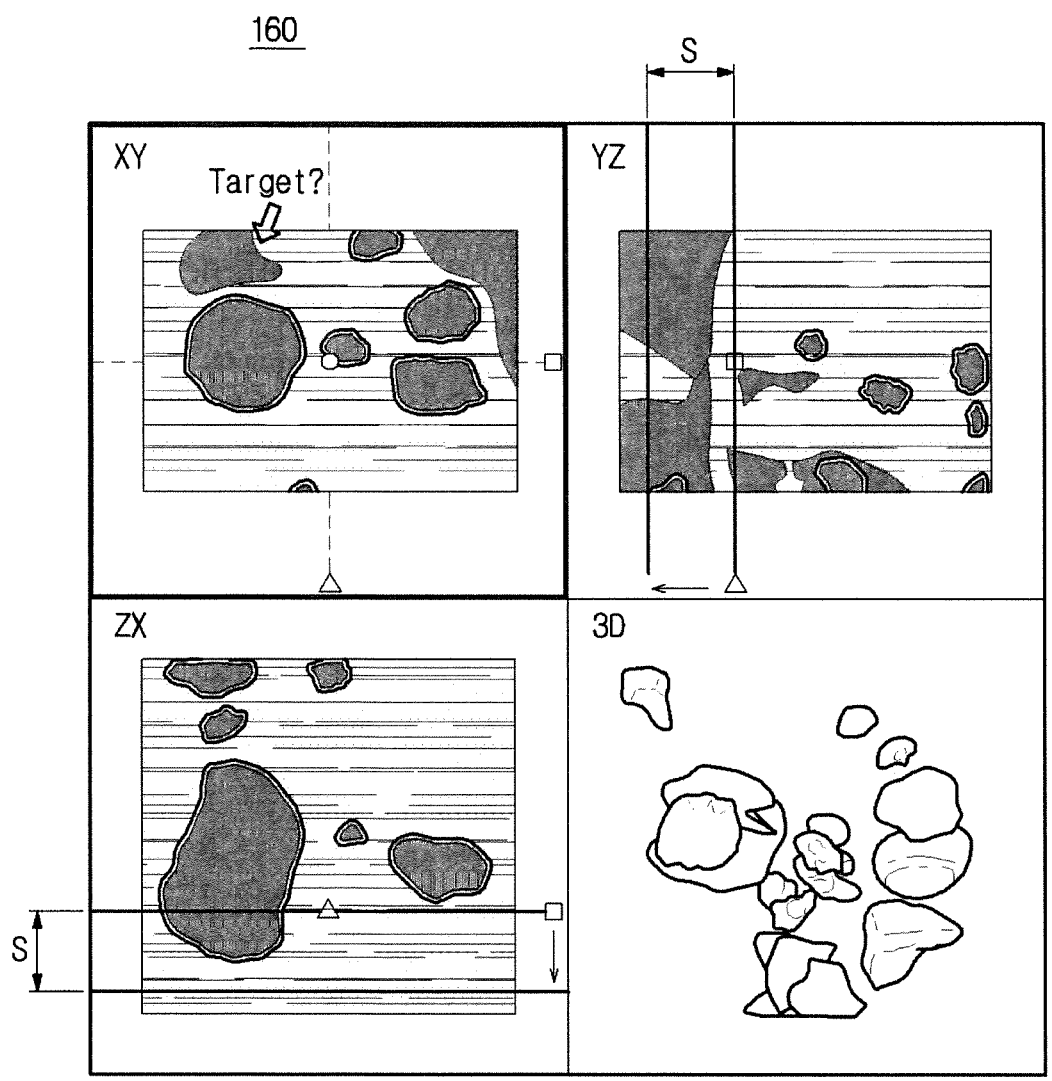
FIGS. 7A and 7B are views for describing an embodiment of a method of displaying a plurality of slice images including a region of interest in an ultrasonic imaging apparatus according to an embodiment of the present disclosure.
Figure 7B:
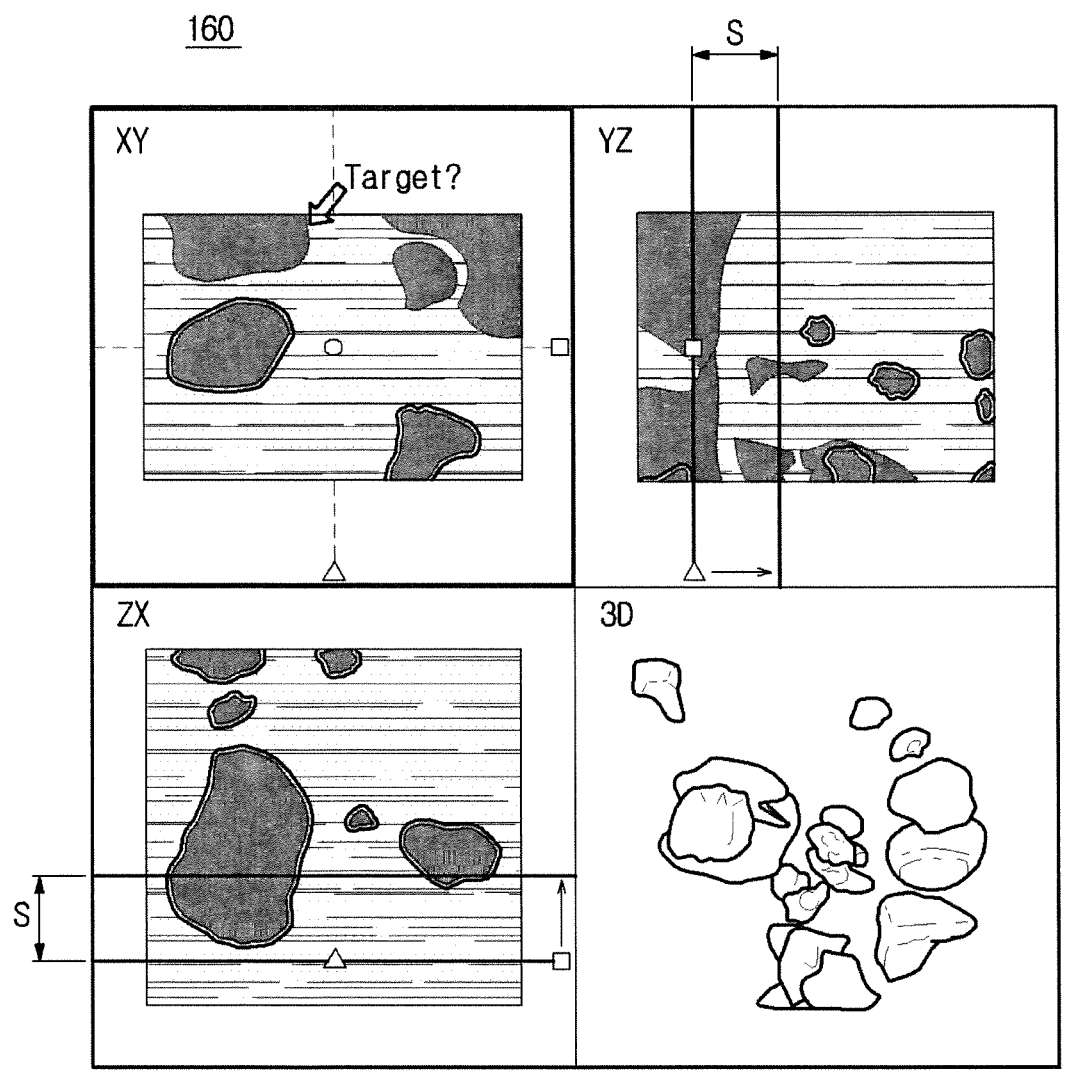

FIGS. 7A and 7B are views for describing an embodiment of a method of displaying a plurality of slice images including a region of interest in an ultrasonic imaging apparatus according to an embodiment of the present disclosure.

As described above, if a slice image displayed on the display unit 160 includes a region of interest, the controller 400 may control the display unit 160 to stop successively displaying a plurality of slice images. As a result, the display unit 160 may keep displaying the slice image including the region of interest that needs to be examined.

In FIG. 7A, a slice image including a region of interest, displayed on the display unit 160, is shown. Since the region of interest is a region that needs to be examined by a user, the display unit 160 needs to provide the user with a lot of information about the region of interest.

Accordingly, the controller 400 may control the display unit 160 to display a plurality of slice images for a section of interest S that is decided by the region of interest. Herein, the section of interest S may be a section decided in advance to provide slice images of the region of interest. After determining the region of interest, the controller 400 may set a section of interest S based on boundary lines of the region of interest.

As shown in FIG. 7B, the display unit 160 may successively display a plurality of slice images of the object for the section of interest S, under the control of the controller 400.

Thereby, the display unit 160 may provide the user with information about a shape and size of the region of interest. Even when a region of interest is determined from an area not exacted as a target, if the display unit 160 displays a plurality of slice images including the region of interest, the user can determine whether the region of interest corresponds to a target.

Figure 8:
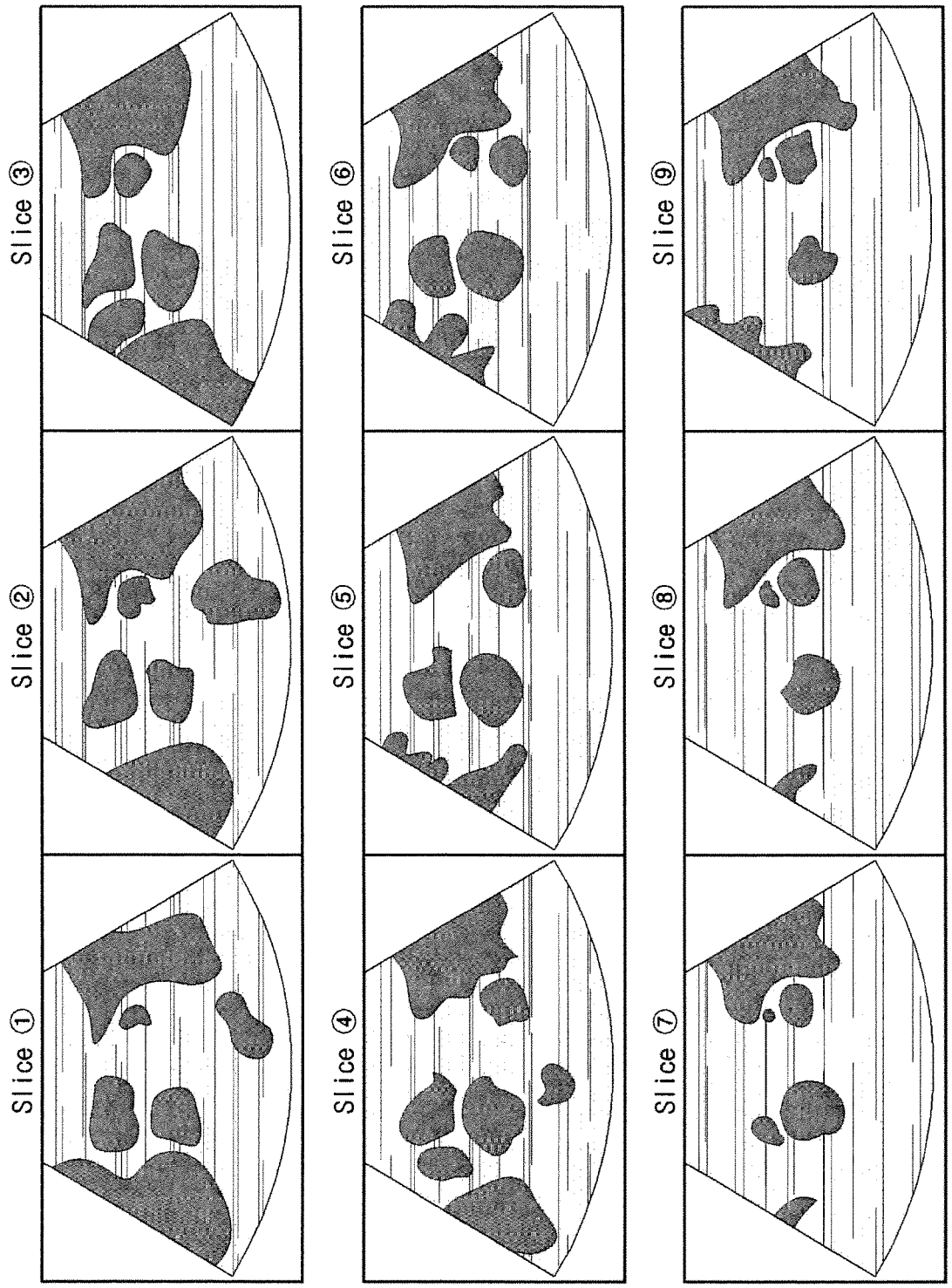
FIG. 8 is a view for describing another embodiment of a method of displaying a plurality of slice images including a region of interest in an ultrasonic imaging apparatus according to an embodiment of the present disclosure.

FIG. 8 is a view for describing another embodiment of a method of displaying a plurality of slice images including a region of interest in an ultrasonic imaging apparatus according to an embodiment of the present disclosure.

FIGS. 7A and 7B show a case in which the display unit 160 successively displays a plurality of slice images including a region of interest, however, the display unit 160 can display a plurality of slice images including a region of interest on one screen.

According to the embodiment of FIG. 8, the display unit 160 can provide a plurality of slice images including a region of interest simultaneously to a user. In this case, since the user can examine a plurality of slice images acquired in various directions at the same time, he/she can compare the features of images of interest at different positions.

After the plurality of slice images including the region of interest are provided to the user, as described above, the input unit 150 may receive at least one of a command for determining the region of interest as a target and a command for canceling an extracted target, from the user.

FIGS. 9A to 9F are views for describing an embodiment of a method of adding a target in an ultrasonic imaging apparatus according to an embodiment of the present disclosure.

In the embodiment of FIGS. 9A to 9F, a region of interest may be a region satisfying a predetermined condition in an area not extracted as a target.

Figure 9A:
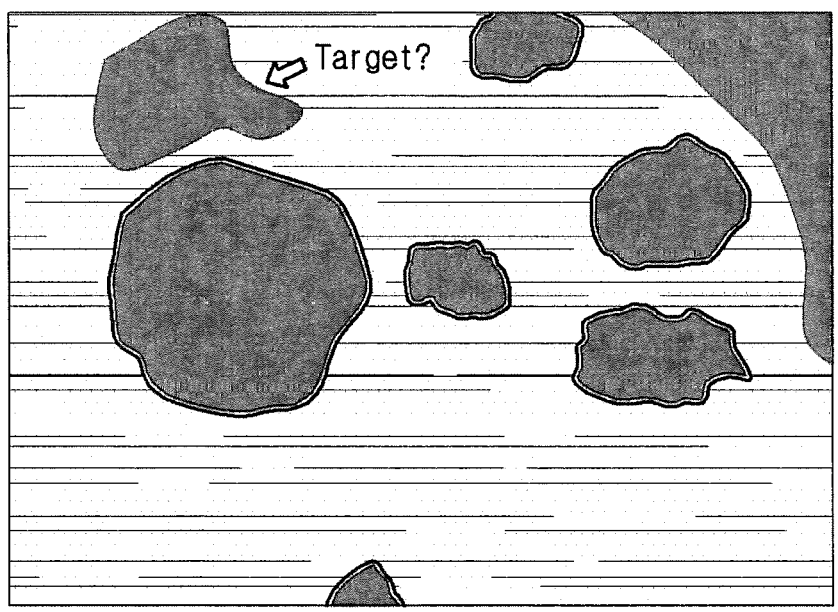
FIGS. 9A to 9F are views for describing an embodiment of a method of adding a target in an ultrasonic imaging apparatus according to an embodiment of the present disclosure.

FIG. 9A shows a slice image including a region of interest, which is one of slice images being successively displayed on the display unit 160. A user may examine the slice image to determine whether the region of interest is a target.

Figure 9B:
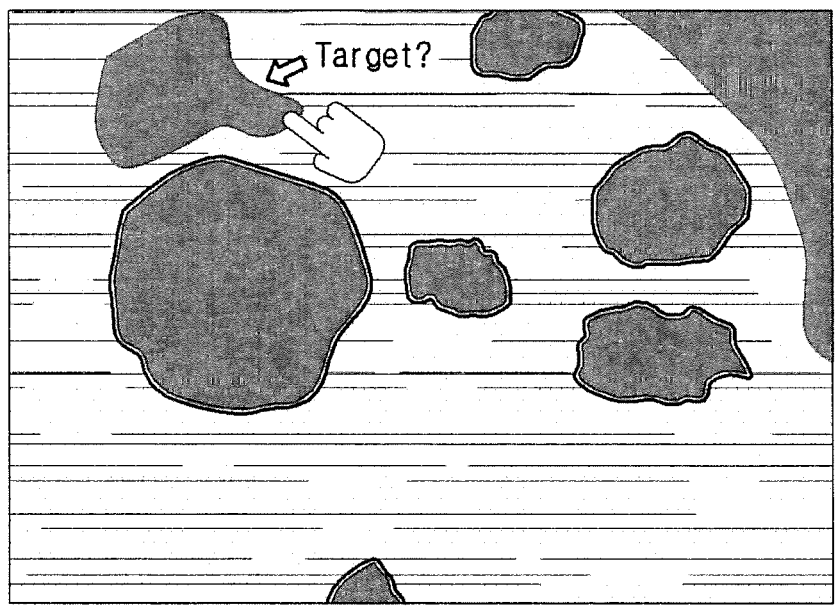

If the user determines that the region of interest is a target, the user may input a command for determining a region of interest as a target through the input unit 150. For example, as shown in FIG. 9B, the input unit 150 may receive a command for selecting a region of interest.

Figure 9C:
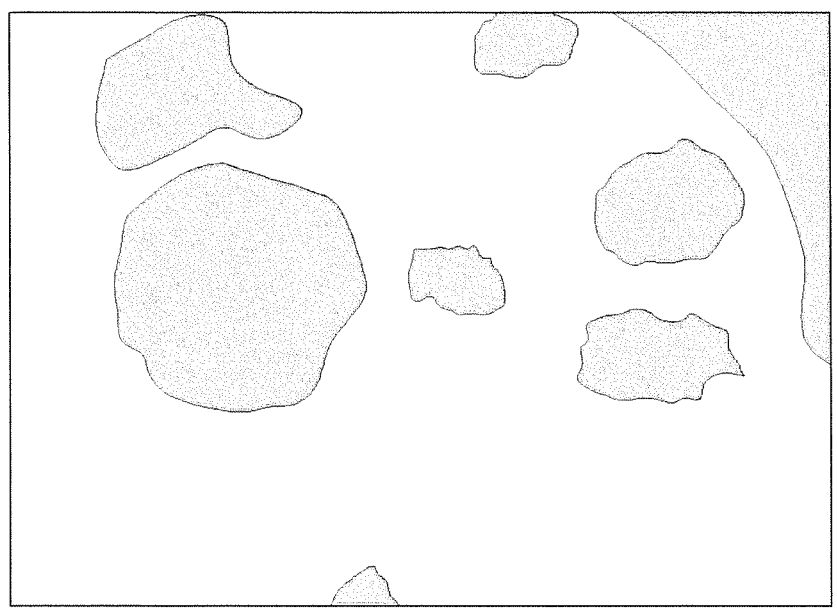
Figure 9D:
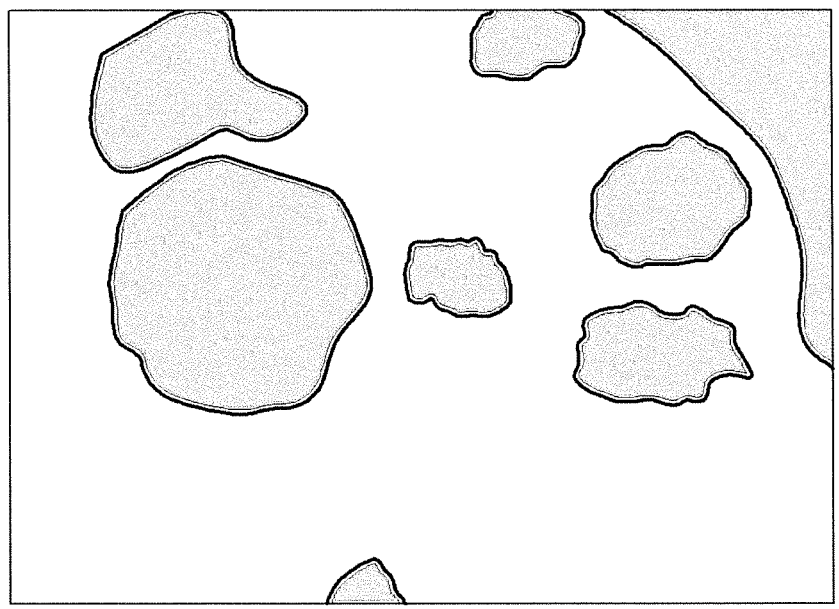
Figure 9E:
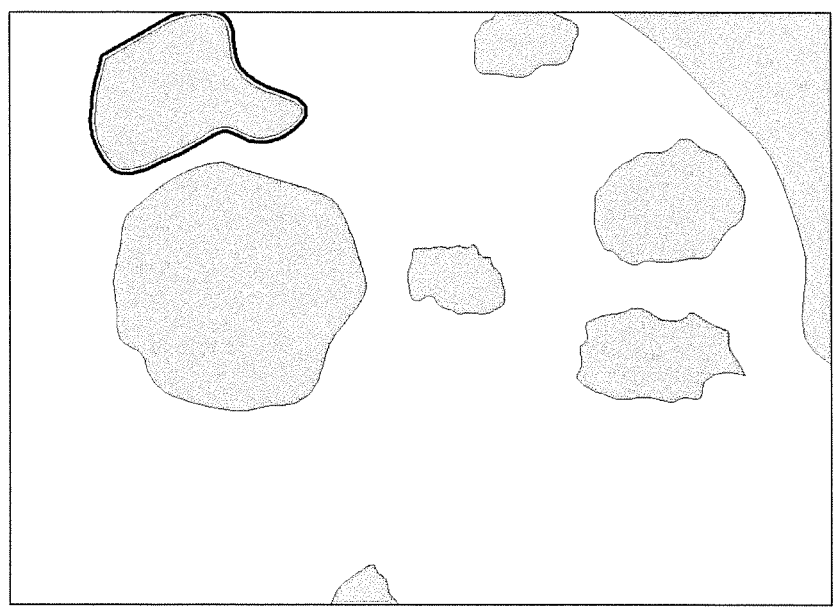
Figure 9F:
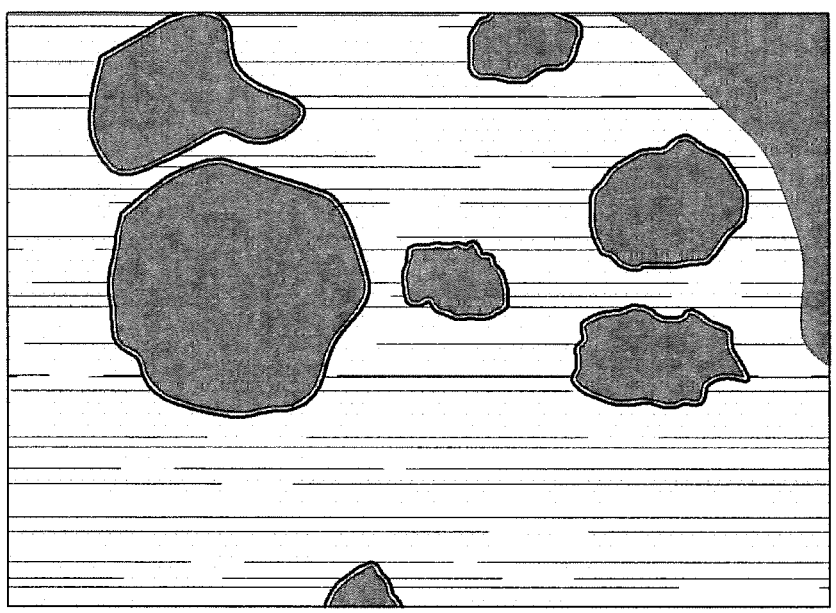

According to the command from the user, the image processor 300 may filter and label the slice image including the region of interest to extract the region of interest determined as a target. FIG. 9C shows an image acquired by filtering the slice image including the region of interest, and FIG. 9D shows an image acquired by labeling the filtered slice image. Also, FIG. 9E shows an image acquired by deleting regions previously extracted as targets from the labeled regions As a result, the display unit 170 may highlight the region of interest newly determined as a target, and display the highlighted, region of interest in the corresponding slice image. For example, the display unit 160 may highlight the boundary line of the region of interest newly determined as a target.

As such, since a region of interest can be added as a target according to a user's input in addition to targets automatically extracted by the image processor 300, the ultrasonic imaging apparatus can provide an environment for more accurate diagnosis.

Meanwhile, the image processor 300 may delete at least one target from extracted targets according to a user's input. If a user inputs a command for cancelling at least one target among extracted targets, the display unit 160 may remove the highlight of the corresponding target.

The above description is given under the assumption that volume data of an object is acquired in real time by the ultrasound probe 200, as shown in FIG. 3A to 3C. However, the ultrasonic imaging apparatus described above is exemplary, and the ultrasonic imaging apparatus may be implemented in various ways within the technical concept of providing volume data of an object to the image processor 300. For example, volume data of an object stored in advance in the ultrasonic imaging apparatus may be provided to the image processor 300, or volume data of an object stored in an external device may be provided to the image processor 300 through communication between the ultrasonic imaging apparatus and the external device.

Figure 10:
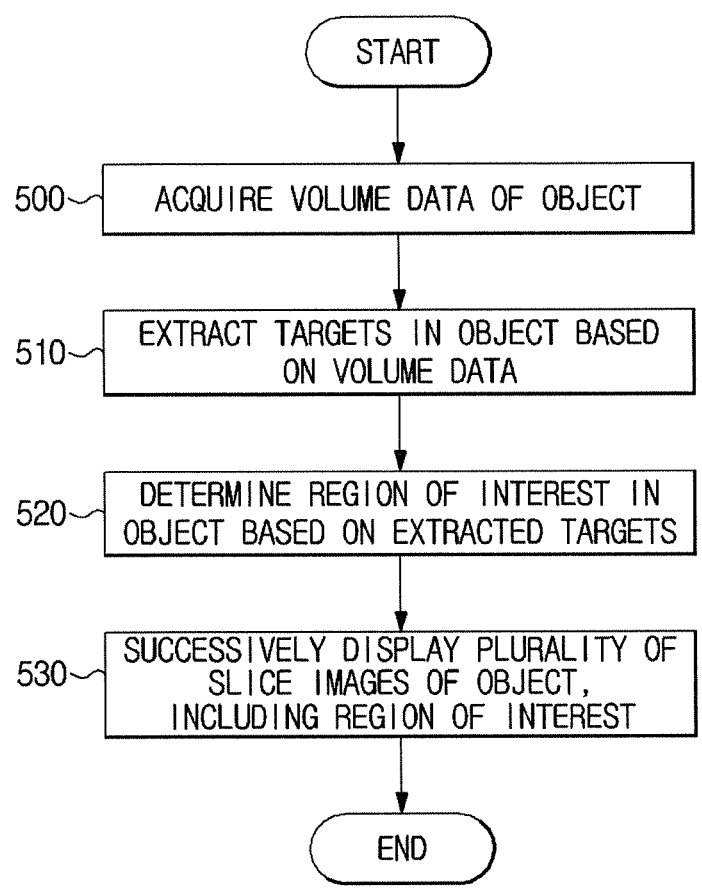
FIG. 10 is a flowchart illustrating a method of controlling an ultrasonic imaging apparatus, according to an embodiment of the present disclosure.

FIG. 10 is a flowchart illustrating a method of controlling an ultrasonic imaging apparatus, according to an embodiment of the present disclosure.

First, ultrasonic waves may be transmitted and received to acquire volume data of an object, in operation 500. At this time, an ultrasound probe may be used to acquire volume data of the object.

Then, one or more targets in the object may be extracted based on the volume data of the object, in operation 510. Herein, the target may be a part of the object, which a user wants to examine through an ultrasound image. For example, if the object is a human's uterus, the target may be a follicle in the uterus.

A method of extracting a target inside an object based on volume data of the object may be at least one of well-known technologies. For example, a volume data area having brightness values in a predetermined brightness range may be extracted as a target. As another example, a target may be extracted by determining whether the size of a volume data area having predetermined brightness values is within a predetermined range.

Then, a region of interest in the object may be determined based on the extracted targets, in operation 520. The region of interest may be a region that needs to be additionally examined by a user in the extracted targets or the other area.

For example, the region of interest may be a target satisfying a predetermined condition among the extracted targets. As another example, the region of interest may be a region satisfying a predetermined condition in the remaining area not extracted as the targets.

Finally, a plurality of slice images of the object, including the region of interest, may be successively displayed, in operation 530. The plurality of slice images may be images about a plurality of sections of the object, which are perpendicular to a predetermined direction.

In this way, by extracting a region of interest automatically, and successively displaying a plurality of slice images including the region of interest, the ultrasonic imaging apparatus can help a user diagnose the region of interest.

Therefore, according to an aspect of the ultrasonic imaging apparatus and the control method thereof as described above, a plurality of slice images of an object, acquired in different directions, can be displayed automatically without a user's manipulations.

Also, according to still another aspect of the ultrasonic imaging apparatus and the control method thereof as described above, a position of a slice image being currently displayed can be marked in another slice image acquired in a different direction so that a user can easily recognize a location, shape, and size of a target.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:
1. An ultrasonic imaging apparatus comprising:
an image processor configured to extract a target in an object based on volume data of the object and generate a plurality of slice images of the object using the volume data;
a controller configured to determine a region of interest in the object based on the extracted target; and a display configured to successively display, by a control of the controller, the plurality of slice images of the object, including the region of interest under controlling of the controller, wherein the controller controls the display to:
successively display the plurality of slice images of the object based on a predetermined frame rate,
successively displays a first plurality of slice images of the object, among the plurality of slice images, for an entire section of the object, the entire section of the object decided with respect to the volume data of the object,
in response to detecting a first slice image including the region of interest, stop the successive display of the first plurality of slice images and display the detected first slice image on a first plane,
after the successive display of the first plurality of slice images has stopped while the detected first slice image is being displayed on the first plane, successively displays a second plurality of slice images which is included in a boundary line of the region of interest on a second plane, among the plurality of slice images,
when the display successively displays a plurality of the first slice images of the object including the region of interest, mark a position of the first slice image being currently displayed in a second slice image of the object, and
display the first plurality of the slice images on the first plane perpendicular to a first direction, and display the second plurality of slice images of the object on the second plane perpendicular to a second direction that is perpendicular to the first direction.

2. The ultrasonic imaging apparatus according to claim 1, wherein the display highlights the extracted target in the plurality of slice images of the object.

3. The ultrasonic imaging apparatus according to claim 1, wherein the display displays the region of interest as a section in the plurality of slice images.

4. The ultrasonic imaging apparatus according to claim 1, wherein the controller determines the region of interest based on a size of the extracted target.

5. The ultrasonic imaging apparatus according to claim 1, wherein the controller determines, as the region of interest, a region satisfying a predetermined condition in the remaining area of the object not extracted as the target.

6. The ultrasonic imaging apparatus according to claim 1, wherein the display displays the plurality of slice images of the object, including the region of interest, at the same time.

7. The ultrasonic imaging apparatus according to claim 1, further comprising at least one of a keyboard, a foot switch, and a foot pedal configured to receive at least one command of a command for determining the region of interest as the target, and a command for cancelling the extracted target.

8. The ultrasonic imaging apparatus according to claim 1, wherein the display marks the position of the first slice image being currently displayed, in a third slice image of the object, wherein the third slice image of the object is perpendicular to a third direction being perpendicular to the first direction and the second direction.

9. The ultrasonic imaging apparatus according to claim 1, wherein the display marks a position of a slice image being currently displayed, in a 3Dimensional (3D) image of the object.

10. A method of controlling an ultrasonic imaging apparatus which comprises a controller configured to perform:
transmitting ultrasonic waves to an object, and obtaining volume data based on echo ultrasonic waves reflected from the object;
extracting a target in the object based on the volume data of the object;
generating a plurality of slice images of the object using the volume data;
determining a region of interest in the object, based on the extracted target;
controlling a display to successively display the plurality of slice images of the object, including the region of interest based on a predetermined frame rate; and
controlling the display to successively display a first plurality of slice images of the object, among the plurality of slice images, for an entire section of the object, the entire section of the object decided with respect to the volume data of the object,
wherein, in response to detecting a first slice image including the region of interest, the controller controls the display to stop the successive display of the first plurality of slice images and to display the detected first slice image on a first plane,
wherein, after the successive display of the first plurality of slice images has stopped while the detected first slice image is being displayed on the first plane, the controller controls the display to successively display a second plurality of slice images which is included in a boundary line of the region of interest on a second plane, among the plurality of slice images,
wherein the successively displaying of the first plurality of slice images comprises:
successively displaying a first plurality of the slice images of the object, including the region of interest; and
marking a position of the first slice image being currently displayed, in a second slice image of the object, and
wherein the controller controls the display to display the first plurality of the slice images on the first plane perpendicular to a predetermined first direction, and to display the second plurality of slice images of the object on the second plane perpendicular to a second direction that is perpendicular to the first direction.

11. The method according to claim 10, wherein the successively displaying of the plurality of slice images of the object, including the region of interest, comprises highlighting the extracted target in the plurality of slice images of the object.

12. The method according to claim 10, wherein the successively displaying of the plurality of slice images of the object, including the region of interest, comprises displaying the region of interest as a section in the plurality of slice images.

13. The method according to claim 10, wherein the determining of the region of interest in the object comprises determining the region of interest based on a size of the extracted target.

14. The method according to claim 10, wherein the determining of the region of interest in the object comprises determining, as the region of interest, a region satisfying a predetermined condition in the remaining area of the object not extracted as the target.

15. The method according to claim 10, further comprising displaying the plurality of slice images of the object, including the region of interest, at the same time, according to an input from a user.

16. The method according to claim 10, further comprising determining the region of interest as the target or cancelling the extracted target, according to an input from a user.

17. The method according to claim 10, wherein the successively displaying of the second plurality of slice images of the object, comprises marking the position of the first slice image being currently displayed, in a third slice image of the object, wherein the third slice image of the object is perpendicular to a third direction being perpendicular to the first direction and the second direction.

18. The method according to claim 10, wherein the successively displaying of the plurality of slice images of the object, including the region of interest, comprises marking a position of a slice image being currently displayed, in a 3Dimensional (3D) image of the object.

* * * * *